US012588824B2

(12) United States Patent
de Vries et al.

(10) Patent No.: US 12,588,824 B2
(45) Date of Patent: Mar. 31, 2026

(54) CARDIAC PULSE WAVE RETRIEVAL FROM AN ELECTRICAL SIGNAL

(71) Applicant: Onera Technologies B.V., Eindhoven (NL)

(72) Inventors: Jantina Catharina de Vries, Eindhoven (NL); Hartmut Schneider, Eindhoven (NL)

(73) Assignee: Onera Technologies B.V., Eindenhoven (NL)

( * ) Notice: Subject to any disclaimer, the term of this patent is extended or adjusted under 35 U.S.C. 154(b) by 548 days.

(21) Appl. No.: 17/616,073

(22) PCT Filed: Jul. 15, 2020

(86) PCT No.: PCT/EP2020/069930
§ 371 (c)(1),
(2) Date: Dec. 2, 2021

(87) PCT Pub. No.: WO2021/009193
PCT Pub. Date: Jan. 21, 2021

(65) Prior Publication Data
US 2022/0296110 A1 Sep. 22, 2022

(30) Foreign Application Priority Data

Jul. 15, 2019 (EP) ..................................... 19186192

(51) Int. Cl.
*A61B 5/021* (2006.01)
*A61B 5/00* (2006.01)
(Continued)

(52) U.S. Cl.
CPC ........ *A61B 5/02108* (2013.01); *A61B 5/0205* (2013.01); *A61B 5/0295* (2013.01);
(Continued)

(58) Field of Classification Search
CPC ..... A61B 5/02108; A61B 5/349; A61B 5/257; A61B 5/0205; A61B 5/0531; A61B 5/6823; A61B 5/7203
(Continued)

(56) References Cited

U.S. PATENT DOCUMENTS

| 10,188,305 B2 * | 1/2019 | Zhang | A61B 5/349 |
| 2006/0173501 A1 * | 8/2006 | Stickney | A61H 31/005 |
| | | | 607/5 |

(Continued)

FOREIGN PATENT DOCUMENTS

| WO | WO-2009072034 A1 * | 6/2009 | ......... A61B 5/02416 |
| WO | WO-2009125349 A2 * | 10/2009 | ......... A61B 5/02208 |
| WO | WO-2012104490 A1 * | 8/2012 | ............. A61B 5/086 |

OTHER PUBLICATIONS

International Search Report and Written Opinion for International Application No. PCT/EP2020/069930, mailed Sep. 23, 2020, (16 pages).

(Continued)

*Primary Examiner* — Michael J Lau
(74) *Attorney, Agent, or Firm* — Kagan Binder, PLLC

(57) ABSTRACT

The present disclosure relates to a method and a system for determining a pulse wave signal (PWS) of a subject. The method (M100) comprises: a step M101) of providing an electrocardiographic (ECG) signal (S2) of a subject (200); a step (M102) of providing an electrical signal (S3) of the subject (200); a step (M103) of determining a collection of points of interest (S2x) in the ECG signal (S2); a step (M104) of determining a collection of specific points (S3x1, S3x2) using the collection of points of interest (S2x); a step (M105) of determining a cleaned electrical signal (S4) based on the collection of specific points (S3x1, S3x2); a step (M106) of determining a pulse wave signal (PWS) by (Continued)

M100 subtracting the cleaned electrical signal (S4) from the electrical signal (S3).

20 Claims, 9 Drawing Sheets

(51) Int. Cl.

| | |
|---|---|
| *A61B 5/0205* | (2006.01) |
| *A61B 5/0295* | (2006.01) |
| *A61B 5/0531* | (2021.01) |
| *A61B 5/257* | (2021.01) |
| *A61B 5/287* | (2021.01) |
| *A61B 5/349* | (2021.01) |

(52) U.S. Cl.
CPC ............ *A61B 5/0531* (2013.01); *A61B 5/257* (2021.01); *A61B 5/287* (2021.01); *A61B 5/349* (2021.01); *A61B 5/6823* (2013.01); *A61B 5/7203* (2013.01); *A61B 2560/0223* (2013.01)

(58) Field of Classification Search
USPC ........................................................ 600/301
See application file for complete search history.

(56) References Cited

U.S. PATENT DOCUMENTS

| | | | | | |
|---|---|---|---|---|---|
| 2008/0058882 | A1* | 3/2008 | Kink | ...................... | A61B 5/053 |
| | | | | | 600/509 |
| 2013/0072806 | A1* | 3/2013 | Zhang | .................. | A61B 5/0205 |
| | | | | | 600/485 |
| 2013/0274623 | A1* | 10/2013 | Zhang | .................... | A61B 5/316 |
| | | | | | 600/517 |
| 2014/0088442 | A1* | 3/2014 | Soykan | ................. | A61B 5/0205 |
| | | | | | 600/483 |
| 2016/0089047 | A1* | 3/2016 | Jonnada | ................. | A61B 5/352 |
| | | | | | 600/521 |
| 2016/0135706 | A1* | 5/2016 | Sullivan | ............... | A61B 5/7267 |
| | | | | | 600/509 |
| 2016/0166155 | A1* | 6/2016 | Banet | .................... | A61B 5/0205 |
| | | | | | 600/382 |
| 2016/0262619 | A1* | 9/2016 | Marcus | ................ | A61B 5/0022 |
| 2016/0287177 | A1* | 10/2016 | Huppert | .............. | A61B 5/6833 |
| 2018/0078159 | A1* | 3/2018 | Edelman | ............ | A61B 5/02141 |
| 2018/0242875 | A1* | 8/2018 | Volpe | ................... | A61B 5/0006 |
| 2018/0360388 | A1* | 12/2018 | Kim | ..................... | A61B 5/7232 |
| 2019/0059752 | A1* | 2/2019 | Botsva | .................. | A61B 5/332 |
| 2019/0076044 | A1* | 3/2019 | Krubsack | .............. | A61B 5/347 |
| 2019/0133483 | A1* | 5/2019 | Xue | ...................... | A61B 5/333 |
| 2019/0183726 | A1* | 6/2019 | McCanny | ............. | A61B 5/347 |
| 2019/0209028 | A1* | 7/2019 | Baxi | ....................... | A61B 5/01 |

OTHER PUBLICATIONS

Moissl et al., "Filtering Respiration in Impedance Cardiography," IFAC Proceedings Volumes, vol. 36, No. 15, 2003, (6 pages).

\* cited by examiner

M100

CARDIAC PULSE WAVE RETRIEVAL FROM AN ELECTRICAL SIGNAL

CROSS-REFERENCE TO RELATED APPLICATIONS

This application claims priority to International Application No. PCT/EP2020/069930, filed Jul. 15, 2020 and titled "CARDIAC PULSE WAVE RETRIEVAL FROM AN ELECTRICAL SIGNAL," which in turn claims priority from a European Patent Application having Ser. No. 19/186, 192.1, filed Jul. 15, 2019, both of which are incorporated herein by reference in their entireties.

TECHNICAL FIELD

The present disclosure relates to a method and a system for providing a pulse wave signal of a subject.

BACKGROUND

Monitoring heart rate and cardiovascular parameters, such as arterial blood pressure, pulse transit time, and arterial stiffness, as well as estimates of left ventricular end diastolic volume pressure or pulmonary capillary wedge pressure, are very important for the management of patients at risk for cardiovascular diseases. These parameters are currently determined using a cardiac pulse wave signal from peripheral arteries, such as the arteries of a finger or an arm. One method is photoplethysmography (PPG), in which a sensor is attached to a finger or an earlobe to obtain information indicative of volume changes in the arteries. Because this method is easy to use and accessible for long term measurements, it is the most widely used method for monitoring heart rate and other cardiovascular parameters.

However, there are several disadvantages with PPG. Artefacts may arise in the pulse wave signal due to movements or varying position. The sensor is also easily dislodged from the patient, which may occur frequently when the patient moves about in his sleep. The sensor may increase discomfort, leading to pain, sleep problems, and even an increase in cardiovascular stress. It is also not possible to quantify the pulse wave signal as it is only indicative of changes in artery volumes and pressure. Moreover, it is not possible to measure blood pressure with PPG. Due to the lack of quantification, repeated longitudinal monitoring is not possible. It is also problematic to accurately determine certain parameters such as the pulse transit time, since additional anatomical measurements, such as the artery length from the heart to the sensor location, would be required to obtain reliable parameter values.

Other alternative methods for monitoring heart rate and cardiovascular parameters may for instance be Doppler and sphygmomanometer. However, these methods do not allow for continuous measuring of blood pressure.

One way of monitoring some cardiovascular parameters is to use bioelectrical impedance analysis (BIA) in which a weak current is sent through tissue and the voltage is measured, thereby allowing the corresponding impedance, i.e. the bio impedance, to be calculated. By BIA, it is possible to measure e.g. cardiac output and stroke volume. However, in general, BIA measurements are confounded by a high technical variability and high spontaneous biological variability leading to difficulties to reliably extract features from a bio impedance signal. Effort to reduce the variability are hampered by a lack of standardized clinical protocols. Also, additional equipment is conventionally necessary to make it possible to retrieve cardiovascular parameters based on the measured electrical signal. Moreover, said measurements are performed on the extremities of a subject, increasing the likelihood of artefacts in the measurements due to the movements of the subject.

Hence, there is a need for an improved method and system for providing a pulse wave signal of a subject, and for monitoring of heart rate and cardiovascular parameters, and a method and system that enables cardiovascular parameters to be accurately extracted from a bio impedance signal.

SUMMARY

It is an object of the present invention to provide an improved solution that alleviates at least some of the drawbacks of present solutions. Furthermore, it is an object to provide a method and a system for providing a pulse wave signal of a subject.

According to a first aspect of the invention, the method for determining a pulse wave signal of a subject is provided. The method may comprise a step of providing an electrocardiographic (ECG) signal of a subject by means of one or more sensors. The method may comprise a step of providing an electrical signal of the subject by means of one or more sensors. The method may comprise a step of determining a collection of points of interest in the ECG signal. The method may comprise a step of determining a collection of specific points in the electrical signal using the collection of points of interest, wherein the determined collection of specific points includes two or more specific points in the electrical signal. The method may comprise a step of determining a cleaned electrical signal based on the collection of specific points. The method may comprise a step of determining a pulse wave signal by subtracting the cleaned electrical signal from the electrical signal. The collection of specific points in the electrical signal may be determined based on timestamps of the collection of points of interest in the ECG signal. At least one of the two or more specific points in the electrical signal for every heartbeat response indicated in the ECG signal may be associated with a timestamp offset in time relative to the timestamp of the corresponding point of interest in the ECG signal.

Two or more of the two or more specific points in the electrical signal for every heartbeat response indicated in the ECG signal may be associated with a timestamp offset in time relative the timestamp of the corresponding point of interest in the ECG signal. All of the two or more specific points in the electrical signal for every heartbeat response indicated in the ECG signal may be associated with a timestamp offset in time relative the timestamp of the corresponding point of interest in the ECG signal.

The electrical signal may be based on a potential difference between different regions of a body of a subject as measured over time in response to a weak current flowing there-between. By weak current, it may be meant a current less than 100 µA, or it may be meant a current on the order of 1-100 µA.

The electrical signal may be a bio-impedance signal, i.e. the potential difference divided by the weak current as measured. The electrical signal may vary in response to relative changes in the blood pressure. The relative changes in the blood pressure may be caused by, for instance, physiological changes, and in particular by breathing. The relative changes in the blood pressure may also be affected by interventions. By "intervention", it may be meant an action or condition which disrupts the physiological state of a subject.

The electrical signal may vary in response to relative changes in the cardiac function, left ventricular end diastolic volume pressure, and pulmonary capillary wedge pressure. The electrical signal may vary in response to positional changes and thus the positional changes in the electrical signal can be used for early detection of cardiovascular problems.

By using an ECG signal and an electrical signal, the method may determine a pulse wave signal of major vessels located in the trunk, such as the pulmonary artery and the aorta, and the left and right heart ventricles. By this method, the pulse wave signal obtained may contain information about the subject, information which pulse wave signals obtained by conventional measurement methods cannot provide. This information may for example be information indicative of physiological changes or states of the subject. In particular, the information may be indicative of different phases of respiration, represented in the pulse wave signal as cyclical amplitude variations over consecutive heartbeat responses. Hence, a reliable variation of the pulse wave amplitude with respiration may be visible.

In order to obtain the pulse wave signal, the method of the present invention may exploit features in the electrical signal that are identified to recur over time in a regular and predictable manner, and more particularly, are identified to recur at a frequency correlating strongly with the heart rate of the subject. In association with these recurring features, specific points may be determined, for example, peaks or dips. For each heartbeat of the subject, the method may determine at least one corresponding specific point. The method may do this for a series of consecutive heartbeat responses, thereby allowing a collection of specific points in the electrical signal to be determined. As stated above, this collection of specific points may then be used when determining the cleaned electrical signal, which in turn may be used to determine the pulse wave signal.

Since each of the recurring features in the electrical signal may be associated with a specific heartbeat of a subject, each of the recurring features may be associated with a specific heartbeat response in the ECG signal. The ECG signal may thus be used to obtain a much better starting guess for determining the specific points in the electrical signal. A starting guess may be a point of interest, i.e. an easily discernible feature in the ECG signal. Such a discernible feature may be a peak in the ECG signal, for instance, the R-peak, the P-peak, or the T-peak, or a dip in the ECG signal, for instance the Q-dip or the S-dip. The method may determine points of interest in a series of consecutive heartbeat responses in the ECG signal, thereby allowing a collection of points of interest in the ECG signal to be determined.

Alternatively, a point of interest may be a location where a slope of a signal reaches a predetermined threshold value. The point of interest may be a location where a first order derivative of the ECG signal is zero. A point of interest may be a location where a second order derivative of the ECG signal is zero.

As stated, the method may comprise steps of providing an ECG signal and an electrical signal of a subject. By this, it may mean that the method may be applied on already measured data representing said signals. It may also mean that the method comprises steps of measuring both the ECG signal and the electrical signal of the subject.

According to one embodiment, the method may comprise a step of providing an electrocardiographic (ECG) signal of a subject. The method may comprise a step of providing an electrical signal of the subject. The method may comprise a step of determining a collection of points of interest in the ECG signal. The method may comprise a step of determining a collection of specific points in the electrical signal using the collection of points of interest. The method may comprise a step of determining a cleaned electrical signal based on the collection of specific points. The method may comprise a step of determining a pulse wave signal by subtracting the cleaned electrical signal from the electrical signal.

According to one embodiment, the collection of specific points in the electrical signal may be determined based on timestamps of the collection of points of interest in the ECG signal. The timestamp of a point of interest in the ECG signal may be close to or the same as a timestamp of a specific feature in the electrical signal. By using a timestamp of a point of interest in the ECG signal as a starting guess, the method may determine the corresponding specific point in the electrical signal more easily. Moreover, the speed of the method may be increased.

According to one embodiment, the two or more specific points in the electrical signal for every heartbeat response indicated in the ECG signal may be determined based on either one point of interest for every heartbeat response indicated in the ECG signal, or a plurality of corresponding points of interest for every heartbeat response indicated in the ECG signal. By this, a pulse wave signal of improved quality may be achieved.

According to one embodiment, points of interest may be determined within a predetermined time window in the ECG signal. The time window may be defined by a start time and a stop time. The start time and the stop time may be specified in terms of time lengths as measured from the timestamp of an easily discernible event for each heartbeat within the ECG signal. For instance, the R-peak may be selected as this event, and the start time and the stop time, given in positive or negative values, then sets out the extent of the time window in which the point of interest is to be located. Alternatives may be the P-peak, the Q-dip, the S-dip, or the T-peak.

By implementing a time window to limit the range in which a point of interest is searched for and determined, the computational speed may be increased.

Moreover, by adjusting the position of the time window, it is possible to target a different point of interest of each heartbeat response in the ECG signal, which in turn may correspond to a different recurring feature in the electrical signal. Moreover, the recurring feature may occur during different time windows in the electrical signal, depending on the location of a measurement device on the subject being measured. For instance, if the measurement device was positioned on the torso of a subject to measure the aorta, the recurring feature of the measured electrical signal may occur in a first time window. If the measurement device was positioned on the torso of a subject to measure the pulmonary artery, the recurring feature of the measured electrical signal may occur in a second time window. If the measurement device was positioned on the torso of a subject to measure the abdominal aorta, the recurring feature of the measured electrical signal may occur in a third time window.

According to one embodiment, the width of the time window may be increased or decreased. This may be done by increasing or decreasing the time difference between the start time and the stop time. The ability of adjusting the width of the time window may be beneficial depending on the level of noise present in the electrical signal. Low levels of noise may allow for the time window to be specified having a narrower width, thereby further increasing the computational speed. High levels of noise may require a widened width, so as to ensure that the desired point of interest is determined reliably within the time interval of the time window.

According to one alternative embodiment, the predetermined time window may be defined by a start time, or a stop time, in conjunction with a time duration. In such a case, the time duration may be specified in terms of a time interval as measured in reference to the start time or the stop time.

According to one embodiment, the collection of specific points in the electrical signal may be local maxima or local minima. For example, by selecting such a local point in the electrical signal as a specific point, the cleaned electrical signal may be determined more accurately and reliably.

According to one further embodiment, a second specific point may be selected in the electrical signal for each point of interest in the ECG signal. The second specific point may be a local maxima or a local minima in the electrical signal. By selecting two specific points in the electrical signal for each point of interest in the ECG signal, the cleaned electrical signal may be based on a denser collection of specific points for the same number of heartbeat responses in the ECG signal, thereby improving the quality of the cleaned electrical signal. A plurality of specific points may be selected in association to each point of interest in the ECG signal, for instance three, four, five, six, seven, eight, nine, ten or more points. By this, an even denser data set is obtained which may further improve the quality of the cleaned electrical signal.

According to one embodiment, the collection of points of interest are determined using a step of R-peak detection. By this, the method may reliably determine a point of interest in the ECG signal, as the R-peak is usually the most easily discernible feature in the ECG signal.

According to one embodiment, the cleaned electrical signal may be determined by means of a step of interpolation based on the collection of specific points. The method may use polynomial interpolation to determine the cleaned electrical signal. By this, the cleaned electrical signal may have a smooth shape. The method may use spline interpolation to determine the cleaned electrical signal. By this, the cleaned electrical signal may be determined more quickly relative the case where polynomial interpolation is used. Moreover, the type of interpolation used may be selected in view of the characteristics of the electrical signal, such as the level of noise, frequency, peak-to-base amplitude etc.

According to one embodiment, the method may comprise a step of filtering the pulse wave signal. By filtering the pulse wave signal, the level of noise may be reduced. This may facilitate extracting information from the pulse wave signal, for instance information pertaining to cardiovascular parameters. The method may comprise an optional step of taking the absolute value of the filtered pulse wave signal. By this, the resulting pulse wave signal may more clearly present information of the physiological changes of the subject during the measurements.

According to one embodiment, the step of providing the ECG signal may involve measuring the ECG signal of the subject. The step of providing the electrical signal may involve measuring an electrical signal of the subject. By these steps of measuring the ECG signal and the electrical signal, the time duration of storing the data representing the ECG signal and the electrical signal may be reduced.

According to one embodiment, the method may determine the pulse wave signal of a subject continuously while the ECG signal and the electrical signal are being measured. By this, it may be possible to monitor the pulse wave signal while the ECG signal and the electrical signal is being measured. Moreover, it may be possible to more easily correlate features in the pulse wave signal with actions or conditions of the subject being measured.

According to one embodiment, the method comprises a step of positioning a measurement device fixedly to a subject to measure the ECG signal and the electrical signal by means of electrodes. By fixedly positioned to a subject, it may be meant that the measurement device is positioned so that it the electrodes are held in fixed positions relative a subject.

The measurement device may be a patch unit incorporating the electrodes. The measurement device may be adapted to be attached to the body of the subject, preferably the torso of the subject. The measurement device may be adapted to be adhesively attached to the torso of a subject. The measurement device may be adapted to be attached to the torso of a subject by means of a strap.

Alternatively, the measurement device may be an implantable device adapted to be implanted in a subject.

By using such a measurement device, a patch unit or an implantable device, it may be less likely to be moved about the intended measurement position during a measurement. The number of resulting artefacts in the ECG signal, the electrical signal, or the pulse wave signal may be reduced. Moreover, the measurement device may be prevented from dislodging from the subject during a measurement. Thus, the risk of missing measurement data may be reduced.

An advantage of using a patch unit is that it may be more easily attached and reattached. Moreover, it may be more form fitted to a subject, thereby being comfortable to wear.

An advantage of using an implantable device is that it may be more easily held in a desired position, thereby reducing the number of artefacts in the determined pulse wave signal. Moreover, an implantable device may be less cumbersome to wear, and it will not be in the way in his everyday life.

A further advantage of this method in respect to using a measurement device as herein described is a more comfortable experience to the subject, which may lead to a better sleep pattern. Moreover, cardiovascular stress may be reduced.

A further advantage is that the measurement device may deliver a more controlled measurement set-up for the determination of cardiovascular parameters, with respect to anatomical measures needed to determine said cardiovascular parameters, such as pulse transit time.

A further advantage is that the measurement device may deliver additional signals relevant for artefact reduction of the said electrical signals. The artefacts may be related but not limited to movements, positional changes, coughing. An advantage of using a patch unit is that it may deliver additional signals for reducing artefacts related to speaking.

A further advantage is that the measurement device may deliver additional signals relevant for the interpretation of said electrical signals. The electrical signals may change with body position, stress or oxygen levels of the body. By monitoring these conditions, the changes in the electrical signals from one condition to the other may provide useful clinical information. For example, changes in cardiovascular parameters from sitting to supine may be used for determining orthostatic dysregulation. Another example, may be the change in pulse wave amplitude in response to elevations in intrathoracic pressure (the Valsalva maneuver) for determining indices of heart failure.

A further advantage is that a pulse wave signal may be determined from both the left and the right side of the heart.

According to one embodiment, the ECG signal and the electrical signal may be measured using the same electrodes.

By this, the measurement device may contain fewer components which may reduce manufacturing cost.

According to one embodiment, the method may comprise a step of adjusting the amplitude of the weak current. By this, recurring features in the electrical signal may be more prominent. Moreover, the amplitude may be adjusted depending on the measurement location of the measurement device. The amplitude may for example be less than 100 µA or be between 1-100 µA. By this, different recurring features may be made more prominent in the electrical signal.

According to one embodiment, the method may comprise a step of varying the frequency of the weak current. By this, recurring features in the electrical signal may be more prominent. Moreover, the frequency may be adjusted depending on the measurement location of the measurement device. The frequency may for example be between 1 kHz and 2 MHz. Hence, different recurring features may be made more prominent in the electrical signal.

According to one embodiment, the measurement device may be positioned so that the determined pulse wave signal is associated with a specific portion of the circulatory system, such as the aorta, the pulmonary artery, or the abdominal artery.

According to one embodiment, the method may comprise a step of calibrating the determined pulse wave signal using a blood pressure measurement. The method may comprise a step of measuring a blood pressure of the subject. The blood pressure measurement may be measured simultaneously as the ECG signal measurement and the electrical signal measurement. By this, the pulse wave signal may be quantified in terms of blood pressure. The pulse wave signal may be calibrated so that the peaks of the pulse wave signal equal the systolic blood pressure. The pulse wave signal may be calibrated so that a baseline of the pulse wave signal equal the diastolic pressure.

According to one embodiment, the method may comprise a step of positioning a pressure measurement device on the subject to measure the blood pressure of the subject. The pressure measurement device may be a blood pressure cuff or other clinically validated devices to obtain the arterial blood pressure non-invasively. The pressure measurement device may be an arterial line catheter.

According to one embodiment, the method may comprise a step of determining cardiovascular parameters from the pulse wave signal. Such cardiovascular may e.g. be blood pressure, pulse transit time, and arterial stiffness.

According to one embodiment, the method may comprise a step of determining a shock index of the subject. By this, vital signs of the subject may be more accurately assessed.

According to one embodiment, the method may comprise a step of presenting the determined pulse wave signal on a display as it is being determined. By this, the pulse wave signal may be inspected during ongoing measurements. This may enable a measurement error to be identified on site, thereby allowing a user to correct the underlying problem causing the measurement error before substantial measurements are being carried out.

According to one embodiment, the method may comprise a step of correcting the ECG signal, the measured electrical signal or the pulse wave signal based on information of a subject's body position. The step of correcting the measured electrical signal or the pulse wave signal may be based on information of a subject's change in body position. This information may be obtained by an accelerometer arranged on the subject's body. The accelerometer may be incorporated into the patch unit.

According to a second aspect of the invention, a system for providing a pulse wave signal of a subject by means of the method according to the first aspect of the invention is provided. The system may comprise a measurement device. The measurement device may comprise one or more sensors adapted to measure the ECG signal and the electrical signal. The plurality of sensors may be electrodes.

According to one embodiment, the ECG signal and the electrical signal are measured using the same electrodes.

According to one embodiment, the measurement device may be a patch unit incorporating the electrodes. The measurement device may be adapted to be attached to the body of the subject, preferably the torso of the subject. The measurement device may be adapted to be adhesively attached to the torso of a subject. The measurement device may be adapted to be attached to the torso of a subject by means of a strap.

Alternatively, the measurement device may be an implantable device adapted to be implanted in a subject.

According to one embodiment, the system may comprise an accelerometer. The accelerometer may be incorporated in the measuring device.

According to one embodiment, the system may comprise a processing unit. The processing unit may be adapted to execute the method according to the first aspect, or any of its corresponding embodiment.

According to one embodiment, the system may comprise a data storage unit. The data storage unit may be adapted to store to the measurements acquired by the measurement unit.

According to one embodiment, the system may comprise a display.

The invention is defined by the appended independent claims, with embodiments being set forth in the appended dependent claims, in the following description and in the drawings.

BRIEF DESCRIPTION OF THE DRAWINGS

The invention will in the following be described in more detail with reference to the enclosed drawings, wherein.

9

Figure 8:
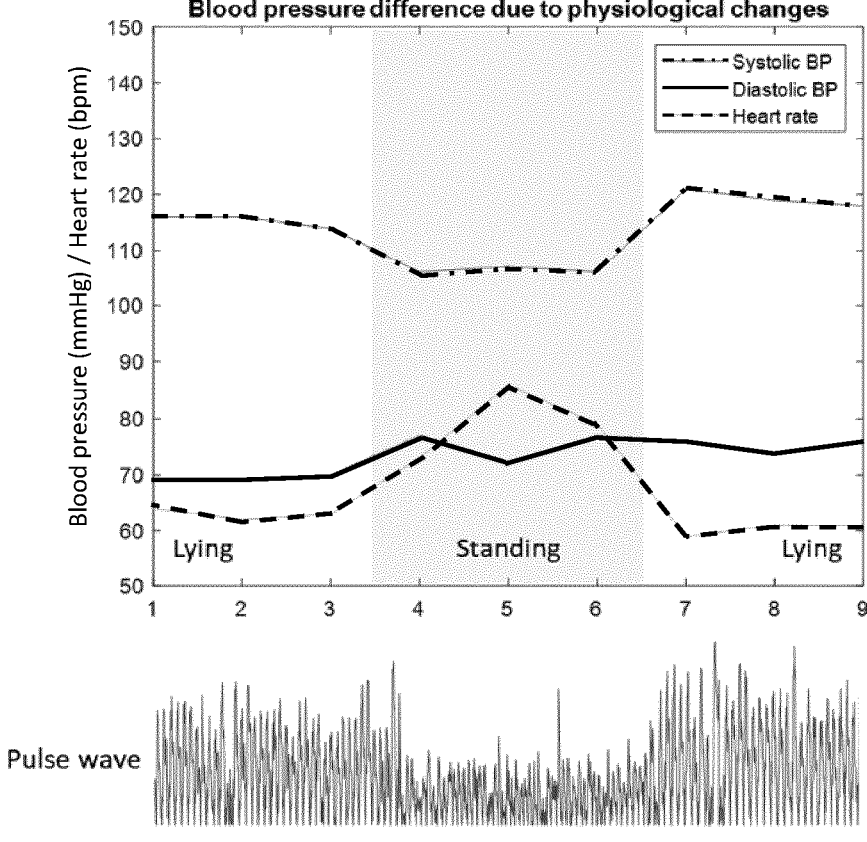
Figure 9:
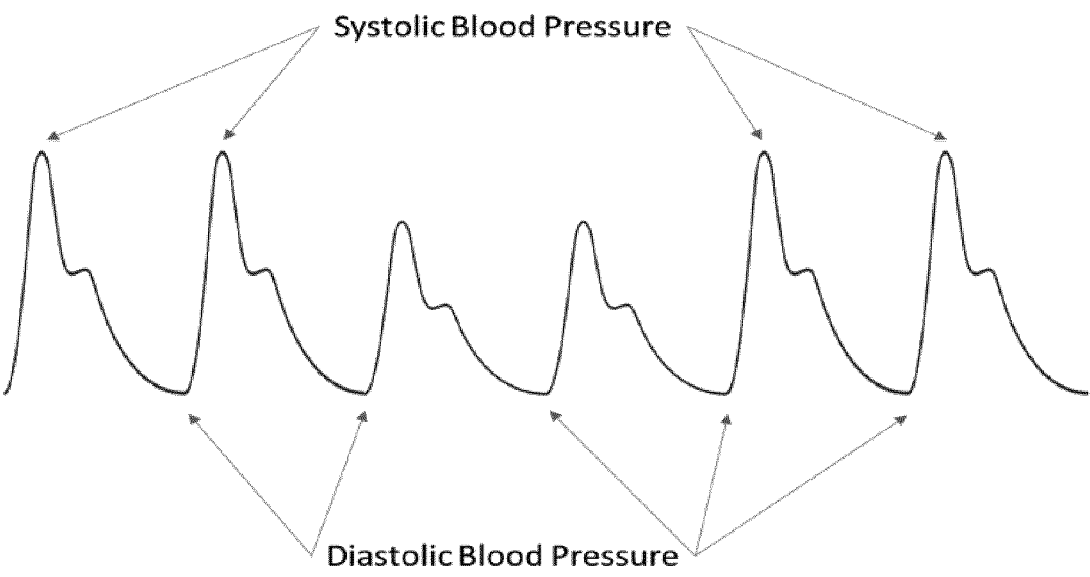
Figure 10:
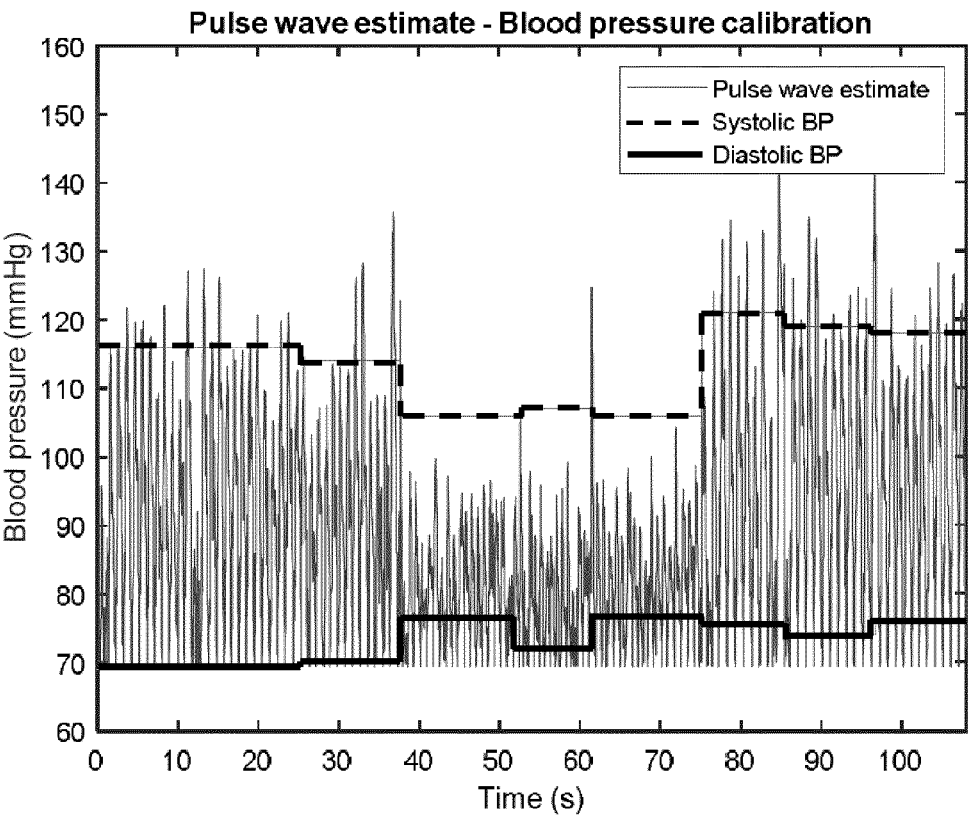
Figure 11A:
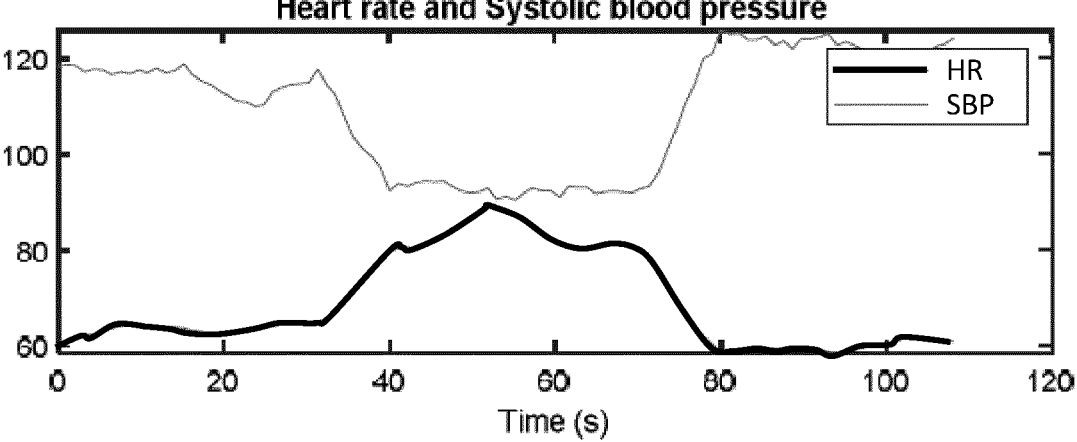
Figure 11B:
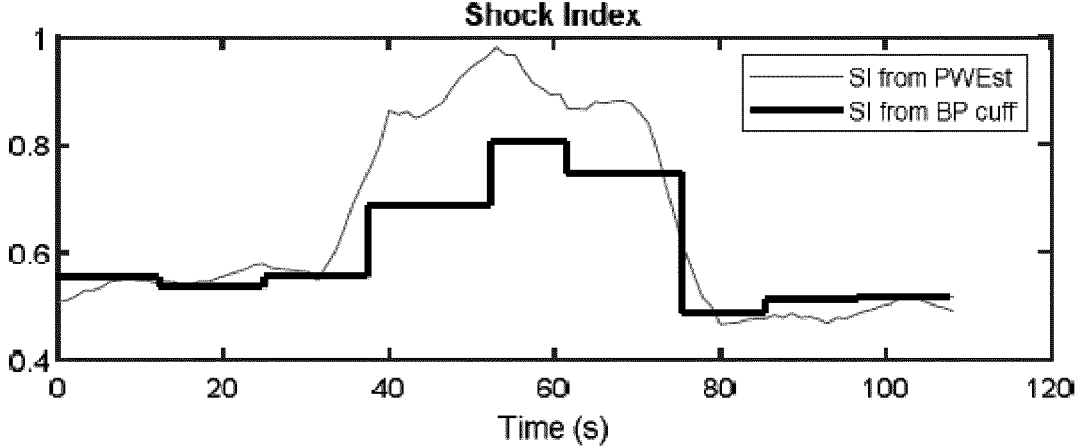
Figure 12:
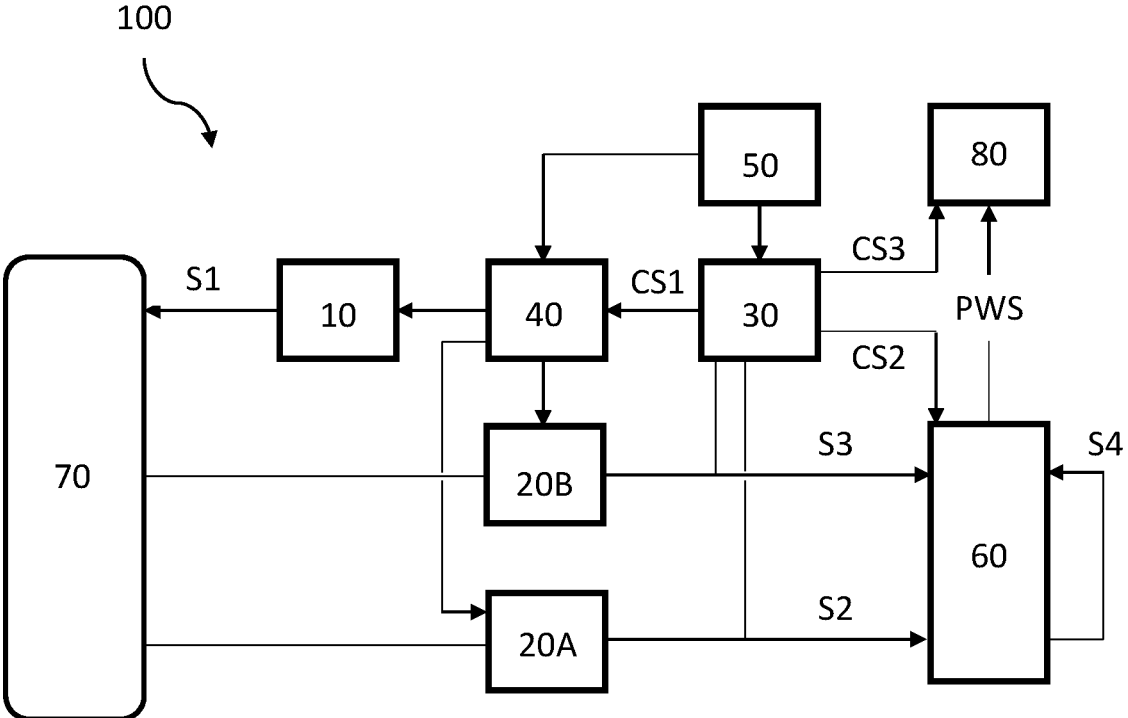
Figure 13A:
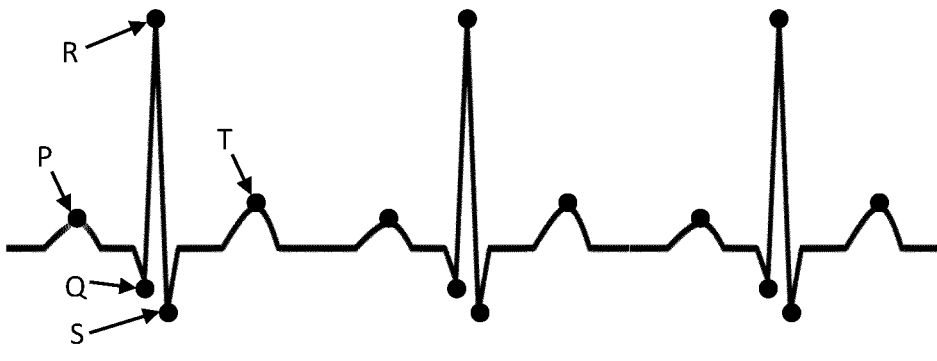
Figure 13B:
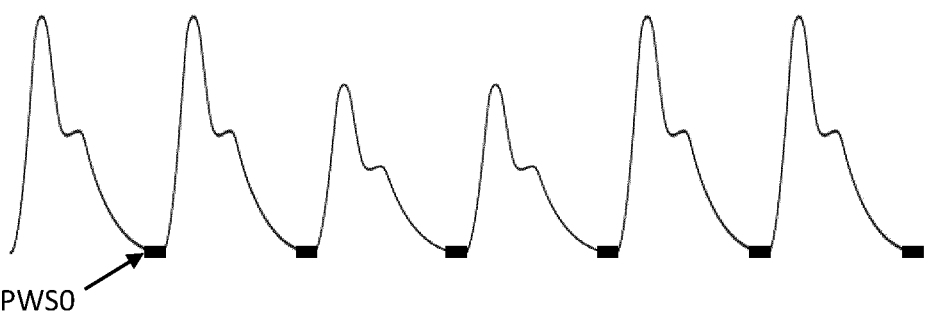
Figure 13C:
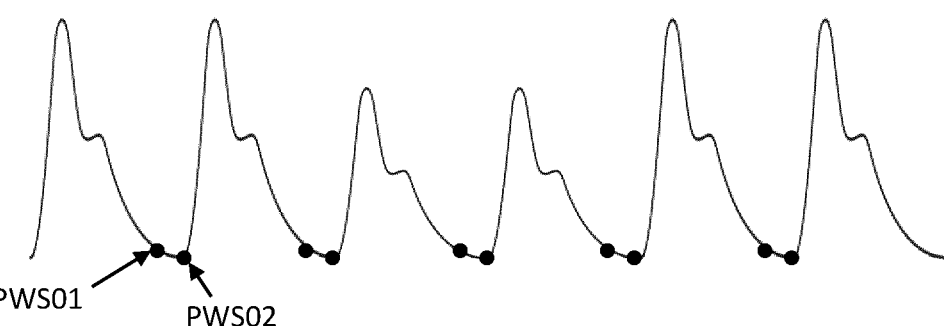
Figure 13D:
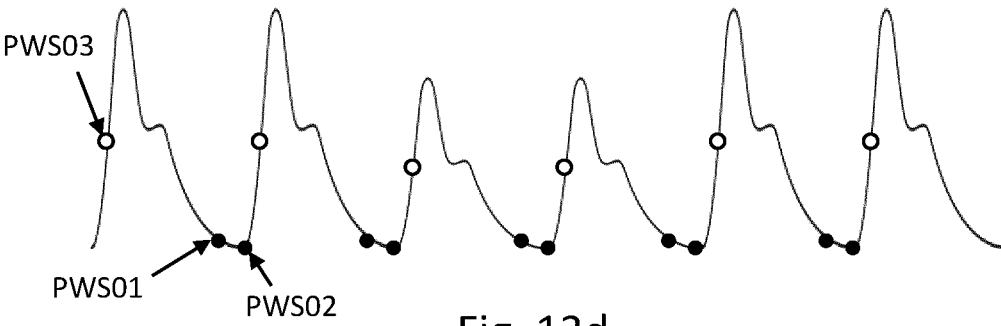

FIG. 8 illustrates changes in the amplitude of the pulse wave signal due to physiological changes, according to one embodiment of the invention;

FIG. 9 illustrates specific points in the pulse wave signal according to one embodiment of the invention;

FIG. 10 illustrates a calibrated pulse wave signal and the systolic and diastolic blood pressure according to one embodiment of the invention;

FIGS. 11a and 11b illustrate the heart rate, systolic blood pressure and shock index, respectively, as derived from the pulse wave estimate according to one embodiment of the invention;

FIG. 12 illustrates a schematic view of a system according to one embodiment of the invention;

FIG. 13a illustrates an ECG signal with points of interest that may be used in determining a pulse wave signal according to some embodiments of the invention, FIGS. 13b-13d illustrate a pulse wave signal indicating how the specific points in the electrical signal are selected according to some embodiments of the invention.

DESCRIPTION OF EMBODIMENTS

The present invention will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements.

Figure 1:
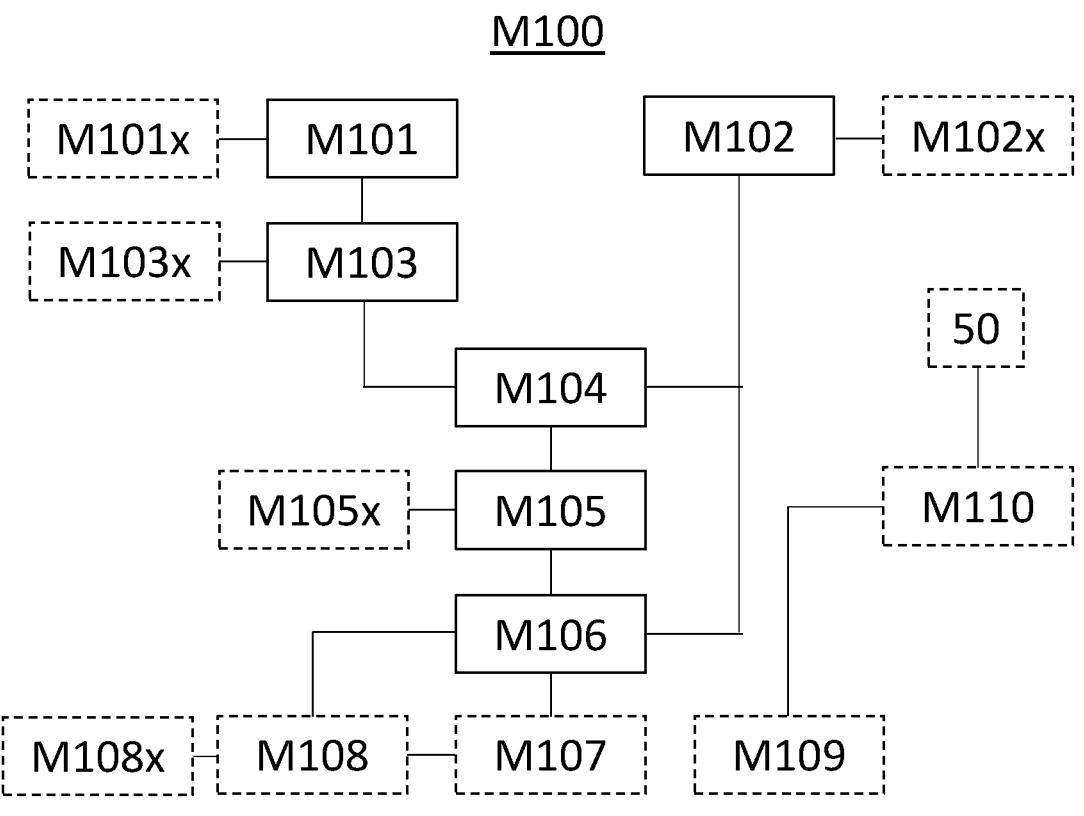
FIG. 1 illustrates a flow diagram of a method according to one embodiment of the invention.

The method M100 for determining a pulse wave signal of a subject is shown in FIG. 1 as a schematic diagram. The method M100 comprises a series of steps which will be detailed in the following. The method M100 may be implemented as an algorithm that is executed during ongoing measurements, the measurements being obtained by a measurement device 1 positioned at a pre-determined position 1a, 1b, 1c on a subject 200, see FIG. 2, or inside a subject 200 in case the measurement device 1 is an implantable device. The method M100 comprises a step M101 of providing an ECG signal S2 of the subject 200, and a step M102 of providing an electrical signal S3 of the subject 200, see FIG. 3. More precisely, the step M101 of providing the ECG signal S2 is realized by a step M101x of measuring the ECG signal S2 of the subject 200. Likewise, the step M102 of providing the electrical signal S3 is realized by a step of M102x of measuring the electrical signal S3 of the subject 200. Both the ECG signal S2 and the electrical signal S3 are measured using electrodes in the measurement device 1. The steps M101x, M102x of measuring the ECG signal S2 and the electrical signal S3 are performed continuously so as to provide the ECG signal S2 and the electrical signal S3, see FIG. 3.

The electrical signal S3 is measured in association with the subject's torso by means of the measurement device 1, and the electrical signal S3 represents the bio-impedance of the subject's torso. The electrical signal S3, i.e. the bio-impedance signal S3, holds information about structures in the trunk, such as the muscles, the lungs, the heart, and the blood vessels located in the trunk. Depending on the location of the measurement device 1, the measured bio-impedance signal S3 carries information which allows distinct portions of the subject's circulatory system to be more characterized. In the following, references will be made to FIG. 1, referencing other steps of the method M100.

Figure 2:
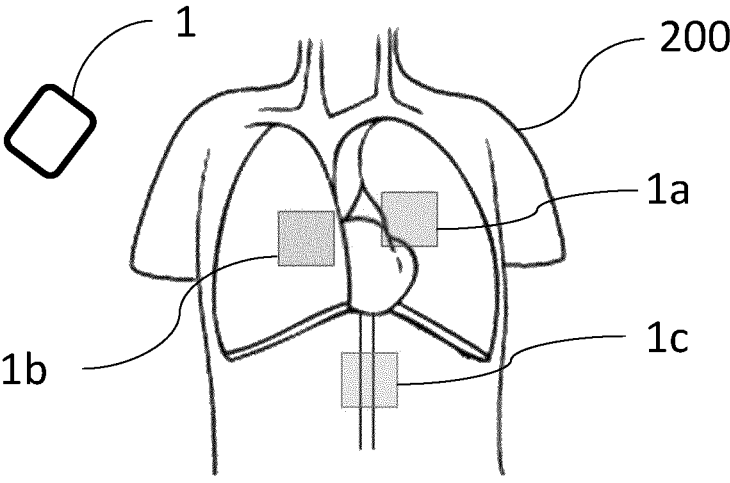
FIG. 2 illustrates examples of patch locations for different measurements according to one embodiment of the invention.

FIG. 2 shows three examples of measurement positions on the subject 200. The measurement device 1 could be positioned to perform measurements of the aorta, e.g. at a location 1a on the left side of the heart. The measurement device 1 could be positioned to perform measurements of the pulmonary artery, e.g. at a location 1b on the right side of the heart. The measurement device 1 could be positioned to perform measurements of the abdominal aorta, e.g. at a location 1c on the stomach of the subject 200.

Figure 3:
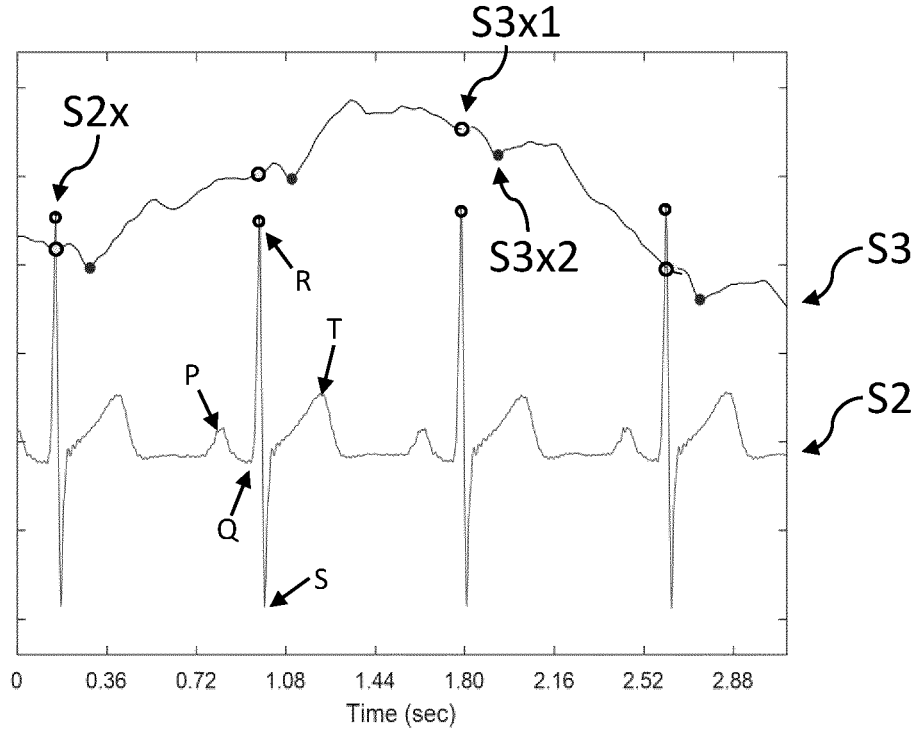
FIG. 3 illustrates a ECG signal and an electrical signal as measured according to one embodiment of the invention.
Figure 4:
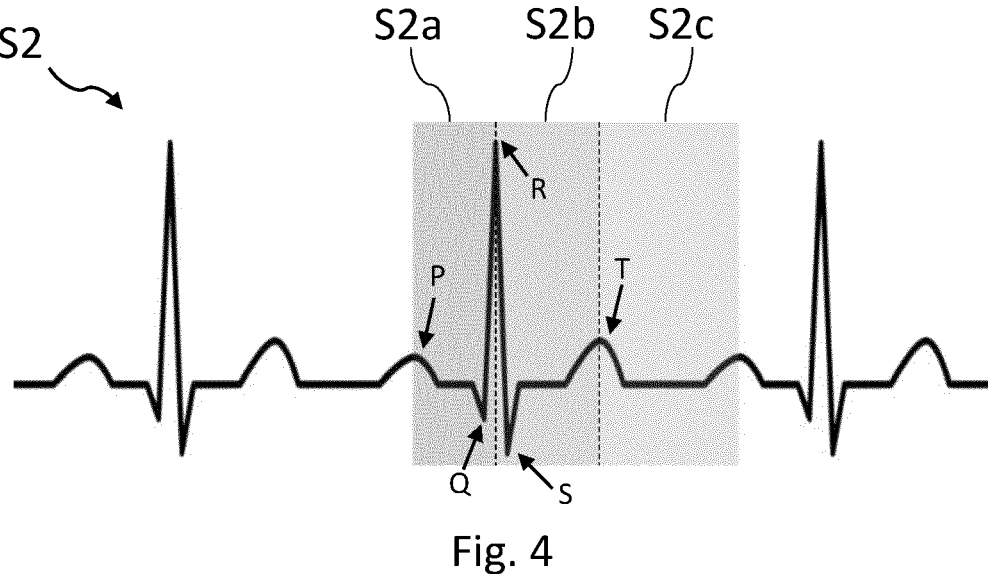
FIG. 4 illustrates an ECG signal and time windows for feature extraction according to one embodiment of the invention.

FIG. 3 depicts measurements of an ECG signal S2 and an electrical signal S3 when the aorta was measured. The horizontal axis represents time and the vertical axis represents Ohm in the case for the bioimpedance signal S3 and voltage in the case for the ECG signal S2. The time interval of the depicted measurement is about three seconds during which four heart beats are registered. As is illustrated in FIGS. 3 and 4, the ECG signal S2 comprises three characteristic components: the P-wave, which represents the depolarization of the atria; the QRS complex, which represents the contraction of the ventricles; and the T-wave, which represents the relaxation of the ventricles. The QRS complex has a noticeable peak—the R-peak. In the vicinity of each timestamp of the R-peaks, two local minima S3x1, S3x2 can be found in the electrical signal S3: one just before or at the timestamp of the R-peak and one a few milliseconds after. The method M100 comprises a step M103 of determining a collection of points of interest S2x in the ECG signal S2. In a preferred embodiment, the point of interest S2x is determined by a step M103x of R-peak detection in which R-peaks are used to form the collection of points of interest S2x. The R-peak detection can be done for example by means of a threshold or peak detection. R-peak detection may be done using the ratio between the slopes of three consecutive points. When the ratio is smaller or greater than a certain threshold, the middle point of the three consecutive points is a local minimum. Then, the method M100 performs a step M104 of determining a collection of specific points S3x1, S3x2 in the electrical signal S3 using the collection of points of interest S2x in the ECG signal S2. The two local minima S3x1, S3x2 are determined using the timestamps at which the R-peaks occur as a starting guess for peak detection. The first local minima may be determined within the first time window S2a and the second local minimum may be determined within time window S2b.

The electrical signal S3 in FIG. 3 corresponds to when measuring the aorta. When measuring other parts of the circulatory system, other points of interest S2x within the ECG signal S2 may be used to find the collection of specific points S3x1, S3x2 within the electrical signal S3. Points of interest S2x within the ECG signal may be associated with predetermined time windows S2a, S2b, S2c within the ECG signal S2, see FIG. 4. The different time windows S2a, S2b, S2c may be used in order to locate the corresponding specific points S3x1, S3x2 in the electrical signal S3 more easily. In the first time window S2a, as alternatives to the R-peak, the peak of the P-pulse or the Q-dip may be used as a point of interest S2x. In the second time window S2b, the S-dip may be used as a point of interest S2x. In the third time window S2c, the peak of the T-pulse may be used. The first time window S2a may correspond to the case where the aorta is measured. The second time window S2b may correspond to the case where the pulmonary artery was measured. The third time window S2c may correspond to the case where the abdominal aorta was measured. Alternatively, the different time windows S2a, S2b, S2c may be used, independently or in combination, for the same type of measurement, for instance when measuring the aorta.

Using the collection of specific points S3$x$1, S3$x$2 in the electrical signal S3, a cleaned electrical signal S4 is then determined in the step M105 (see FIG. 1) of the method M100. This is done by a step M105$x$ of interpolating between the collection of specific points S3$x$1, S3$x$2 found in the electrical signal S3. The interpolation may be done using e.g. cubic interpolation.

Figure 5A:
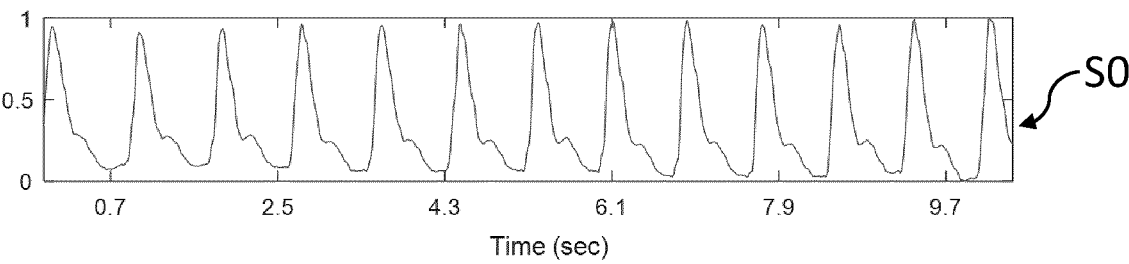
FIG. 5a illustrates a photoplethysmography from the peripheral arteries of the finger according to one embodiment of the invention.
Figure 5B:
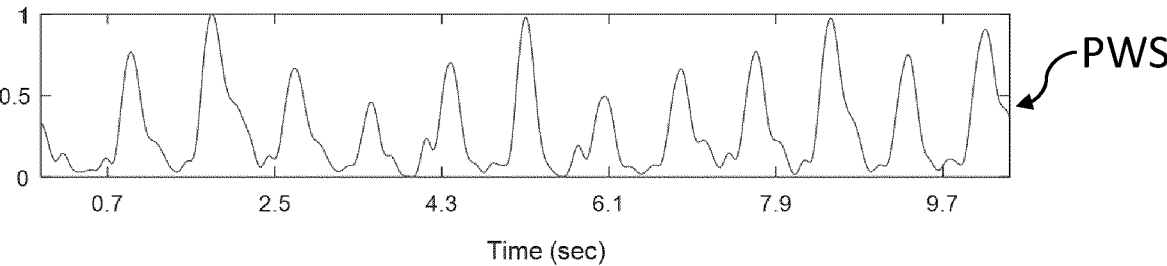
FIG. 5b illustrates a pulse wave signal from the electrical the electrical signal according to one embodiment of the invention.
Figure 5C:
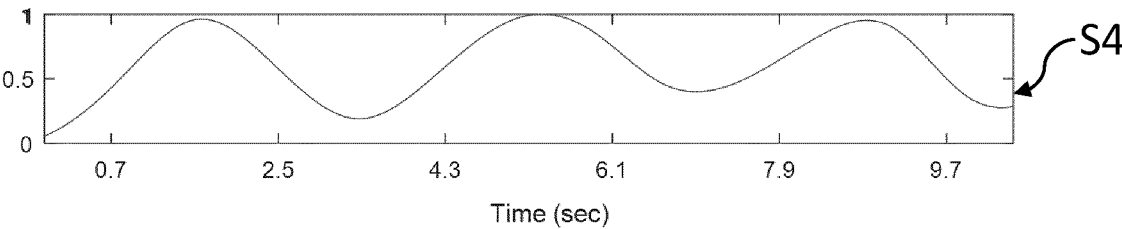
FIG. 5c illustrates a cleaned electrical signal according to one embodiment of the invention.

In a further step M106 of the method M100 (see FIG. 1), the pulse wave signal is determined by subtracting the cleaned electrical signal S4 from the electrical signal S3. In a step M107 (see FIG. 1), the pulse wave signal PWS is filtered and it's absolute is calculated, and and this resulting pulse wave signal PWS is depicted in FIG. 5$b$. For the sake of comparison, a photoplethysmography S0 (i.e. a pulse wave signal) from the peripheral arteries of the finger is shown in FIG. 5$a$. The cleaned electrical signal S4 obtained by the step M105 is shown in FIG. 5$c$. In each of the FIGS. 5$a$-5$b$, the horizontal axis represents time and the vertical axis represents the normalized amplitude of each signal.

Figure 6:
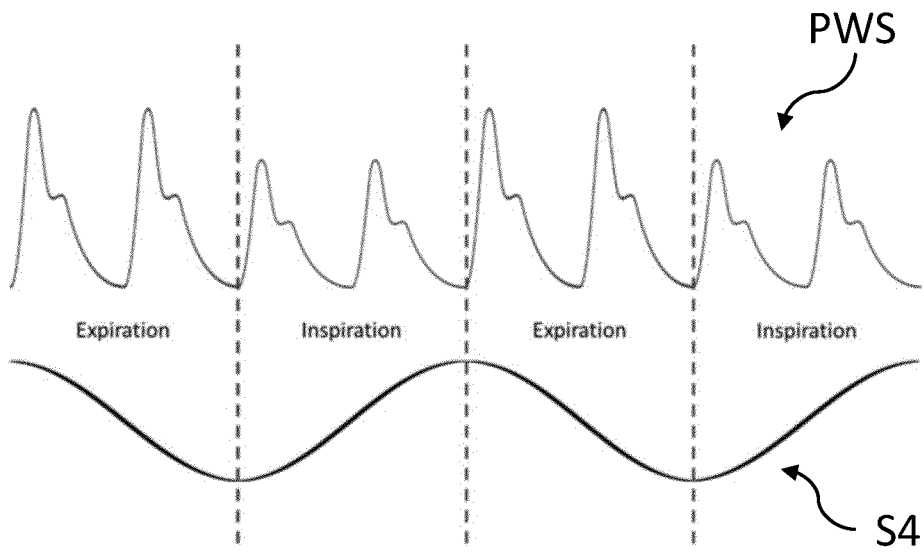
FIG. 6 illustrates changes in the amplitude of the pulse wave signal in view of a breathing pattern according to one embodiment of the invention.

As can be seen in FIG. 5$b$, the pulse wave signal PWS shows cyclical changes in the amplitude as compared to the pulse wave signal S0 obtained from photoplethysmography in FIG. 5$a$. These cyclical changes in amplitude correspond to changes in blood pressure due to pressure differences in the trunk during breathing and due to physiological changes. During inspiration and expiration, the lungs expand and contract respectively. Due to this, there is a change in the pressure the lungs exert on surrounding tissue, such as the surrounding blood vessels. During inspiration the lungs expand, causing the lungs to exert more pressure on the surrounding blood vessels. This results in a lower blood pressure in the surrounding blood vessels, and therefore a reduced amplitude in the pulse wave signal PWS. A schematic of the change in the amplitude of the pulse wave signal is shown in FIG. 6. As is clear from FIG. 5$a$, this cyclical change in the amplitude is not visible in pulse wave signals obtained by conventional measurement methods.

As has been previously detailed, the pulse wave signal PWS contains information that may be used to determine cardiovascular parameters. One way of extracting information from a pulse wave signal PWS is to determine a pulse amplitude ratio PAR. The pulse amplitude ratio PAR gives an indication of the strength of an intervention, i.e. an action or a condition disrupting the physiological state of a subject. For instance, an intervention may be a physical activity, such as standing up from a sitting position. Other types of interventions may for instance be obstruction sleep apnea; central sleep apnea; hypoxia, and sympathetic stimuli.

Figure 7:
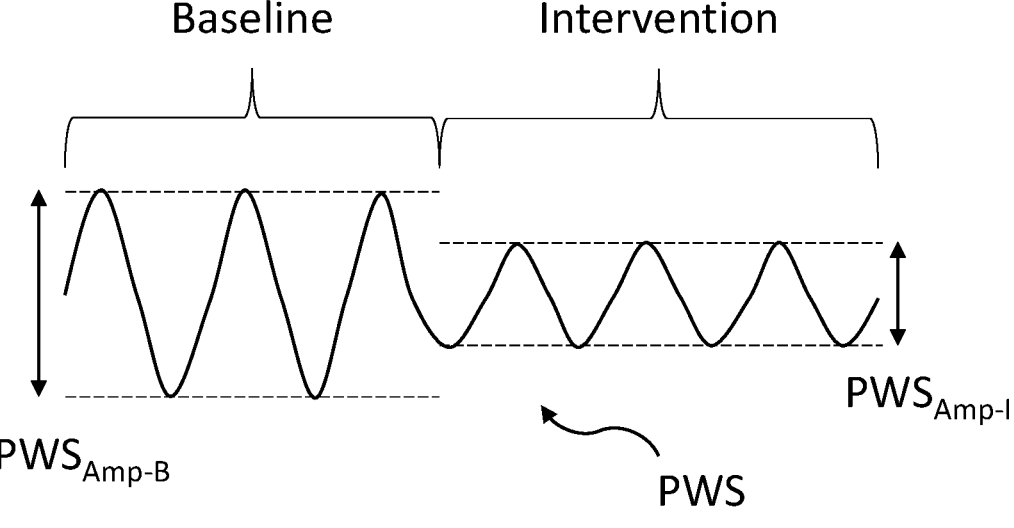
FIG. 7 illustrates how an intervention may affect the amplitude of the pulse wave signal according to one embodiment of the invention.

The pulse wave ratio is defined as the ratio between a pulse wave amplitude during an intervention and a baseline pulse wave amplitude, i.e. a pulse wave amplitude corresponding to a normal or resting state of the subject. Hence, the pulse amplitude ratio PAR is calculated as $$PAR = \frac{PWA_{Amp-I}}{PWA_{Amp-B}},$$

where $PWA_{Amp-I}$ is the amplitude during the intervention and $PWA_{Amp-B}$ is the baseline amplitude. This is illustrated in FIG. 7 in which a pulse wave signal PWS characterized during two separate time durations, wherein the pulse wave amplitude PWA during the first time duration is set as the baseline amplitude, $PWA_{Amp-B}$, and wherein the pulse wave amplitude PWA during the second time duration is set as the intervention amplitude $PWA_{Amp-I}$. As can be seen in FIG. 7, the pulse wave amplitude PWA decreases during an intervention. Moreover, the pulse amplitude ratio PAR may be defined to range in value between 0≤PAR≤1. However, it can also be that the intervention causes for a higher PWA. In such a case the PAR will be >1.

The pulse amplitude ratio PAR may thus give an indication of the strength of the impact experienced by the subject given some intervention. Assuming now that the PAR ranges between 0 and 1, if the value is high, i.e. close to or equal to 1, then the subject from which the pulse wave signal was extracted was not particularly affected by an intervention. If the value is low, i.e. close to or equal to 0, then the subject from which the pulse wave signal was extracted was very much affected by said intervention.

Moreover, the pulse amplitude ratio PAR may be determined from a pulse wave signal PWS in which an intervention is held constant. Also, the pulse amplitude ratio PAR may be determined from a pulse wave signal PWS in which an intervention is changing over time. Data regarding the pulse wave signal PWS from a plurality of subjects may be collected. The data may be organized with respect to age, gender, height, weight, behaviors, interventions etc. Then, when a new measurement of a pulse wave signal PWS from a subject is acquired, the pulse amplitude ratio PAR of the acquired pulse wave signal PWS may be compared with a pulse wave ratio PAR value typical of subjects with similar age, gender, height, weight, behaviors, interventions as the newly measured subject.

When analysing the pulse wave amplitude of a subject, and in turn the pulse amplitude ratio PAR, it may be useful to consider arterial compliance C. According to a classic definition of arterial compliance, it is defined as the change in arterial blood volume $\Delta V$ due to a given change in arterial blood pressure $\Delta P$. Thus, the arterial compliance C is calculated as $$C = \frac{\Delta V}{\Delta P}.$$

Arterial compliance C can be said to represent the elasticity of the arteries of the subject, wherein a higher elasticity indicates a healthier subject. The arterial compliance C, i.e. the elasticity of arteries, may diminish due to irregular health conditions, and may diminish also with age and menopause. A subject having a low value of PAR may likely have a low value in arterial compliance C also. Hence, the method may thus give an indication regarding the arterial compliance also, without making any blood pressure measurements.

Moreover, the PAR may be extracted from an uncalibrated pulse wave signal PWS and a calibrated pulse wave signal PWS, calibrated with respect to, for instance, blood pressure. Information from a calibrated pulse wave signal PWS may be used in determining blood flow resistance in a subject. The resistance R may be determined as a change in blood flow, $\Delta Q$, multiplied by a change in pressure, $\Delta P$, i.e.

$$R = \Delta Q \cdot \Delta P.$$

The change in pressure, $\Delta P$ may be acquired from the calibrated pulse wave signal PWS. The change in blood flow $\Delta Q$ may be measured by a flow probe or a sensor. The change in blood flow $\Delta Q$ may be measured by taking the derivative of the PWS. A change in resistance may indicate, for example, an internal bleeding in which case the resistance decreases due to a decreased pressure, or a clogging of arteries in which case the resistance increases due to a decreased pressure.

FIG. 8 shows an example of a change in the amplitude of an uncalibrated pulse wave signal PWS due to physiological changes. The horizontal axis represents time and the vertical axis represents blood pressure in mmHg. FIG. 8 shows the physiological response to the Schellong test (tilt-table-test), during which a subject is lying down, standing up, and lying down again. When the subject stands up, the systolic blood pressure drops from about 115 mmHg to about 105 mmHg, and the heart rate rises to compensate for the lower blood pressure. When the subject is lying down again, the blood pressure and the heart rate go back to the same level before the subject was standing. FIG. 8 shows that the pulse wave signal obtained by this method holds information about this physiological change.

The pulse wave signal PWS indicates pressure differences. In order to quantify the pulse wave signal PWS in terms of pressure, a reference signal is required to calibrate the pulse wave signal. A step M108 of calibrating the determined pulse wave signal PWS is done using a blood pressure measurement (see FIG. 1). The blood pressure measurement may be obtained in a step M108x using a certified blood pressure measurement device, such as a blood pressure cuff and an arterial line catheter. The blood pressure cuff is a non-invasive measurement device, but it cannot measure the blood pressure continuously. The arterial line measures the blood pressure continuously in the arteries, however this is an invasive method. For the calibration, test subjects are needed to measure the blood pressure using the method described in this invention and using one of the above-mentioned pressure measurement devices simultaneously. The subject should be seated and in rest for a minimum of five minutes. The subject is wearing both the measurement device 1 and a pressure measurement device.

In the case the pressure measurement device is the blood pressure cuff, the blood pressure is measured several times in succession, e.g. three times. The pulse wave signal PWS is determined continuously by a processing unit based on the ECG signal measurements and the electrical signal measurements as measured by the measurement device 1. Then, the pulse wave signal PWS is calibrated such that the peaks in the pulse wave signal PWS equal the systolic blood pressure, and the baseline of the pulse wave signal equal the diastolic pressure, as shown in FIG. 9. The time period during which the blood pressure is measured using the cuff can be marked in the pulse wave signal PWS. Over this time period, the average peak height of the peaks during exhalation could be determined, as well as the average baseline value. The average peak height in the pulse wave signal PWS equals the average systolic pressure as measured by the blood pressure cuff and the average baseline value equals the average diastolic pressure. FIG. 10 shows a calibrated pulse wave signal using the systolic and diastolic blood pressure as measured using a blood pressure cuff.

In case the pressure measurement device is the arterial line catheter, the pulse wave signal PWS is determined continuously by the processing unit based on the ECG signal measurements and the electrical signal measurement acquired by the measurement device, and the blood pressure measurement acquired by the pressure measurement device. The blood pressure is measured simultaneously for a specific time period (for example 5 minutes). Over this time period, the average peak height is determined, as well as the average baseline value in both signals. The average peak height and baseline value of the pulse wave signal obtained by the method M100 then equal the average peak height and baseline of the reference signal.

The method M100 may also comprise a step M109 of determining a cardiovascular parameter. Cardiovascular parameters may for instance be arterial blood pressure, pulse transit time, arterial stiffness, as well as estimates of left ventricular end diastolic volume pressure or pulmonary capillary wedge pressure.

One way of accurately assessing a subject's vital signs is to use the shock index, SI, which is calculated as the heart rate divided by the systolic blood pressure. The shock index has shown to give more information than assessing the heart rate and the systolic blood pressure apart from each other. It is a very powerful parameter for trauma patients since it is accurate and since it is easy to measure the heart rate and blood pressure. The SI can e.g. be used to predict several stroke outcomes and to predict whether a patient is a high-risk septic patient.

The SI is calculated by the following formula:

$$SI = \frac{HR}{SBP} = \frac{\frac{60}{T_{RR}}}{SBP}$$

wherein HR is the heart rate, SBP is the systolic blood pressure. The heart rate HR can be derived from the ECG-signal S2 by first determining the peak-to-peak time period, $T_{RR}$, i.e. the time between two consecutive R-peaks. In FIG. 11a, the heart rate and systolic blood pressure are shown, and in FIG. 11b, the SI in the bottom graph together with SI as measured from the data of the blood pressure cuff for comparison.

FIG. 12 illustrates an electronic system 100 for acquisition of an ECG signal S2 and an electrical signal S3. The system 100 is configured to generate a current signal S1 that is to be applied to a subject 200 by means of electrodes 70 and to measure an electrical signal S3 by means of electrodes, thereby providing information of the bioimpedance of the subject 200. The electrical signal S3 may be further processed, e.g. for monitoring respiration of the subject. The system 100 is configured to adaptively change settings in order to maintain desired data quality of the measured electrical signal S3.

As shown in FIG. 12, the system 100 comprises a current signal injection module 10. The current signal injection module 10 may be configured to generate and output the current signal S1, which is to be applied to the subject 200 by means of electrodes 70. The current signal injection module 10 may comprise a current source for generating the current signal S1. The current signal injection module 10 may further comprise settings, which may be used for controlling the current signal S1 being generated and output by the current injection module 10.

The current signal injection module 10 may be configured to output an AC current signal. The settings of the current signal injection module 10 may control an amplitude and a frequency of the generated current signal S1.

The system 100 further comprises an electrocardiography (ECG) signal measurement module 20A. The ECG signal measurement module 20A may be configured to receive a first set of voltage signals representing the electrical activity of a subject's heart. The ECG signal measurement module 20A may be configured to extract a measured ECG signal S2 from the received first set of voltage input signals. The electrocardiography signal measurement module 20A may comprise settings, which may be used for controlling the extraction of the ECG signal S2 from the received first set of voltage input signals. For instance, a gain of the measured ECG signal S2 may be controlled by the settings.

The ECG signal measurement module 20A may be configured to process the received first set of voltage input signals, e.g. by filtering the input signals, in order to extract relevant information. The filtering of the input signals may also be controlled by settings of the electrocardiography signal measurement module 20A or may be performed according to a fixed set-up.

The ECG signal measurement module 20A may output the measured ECG signal S2, which may be used for determining a condition of the subject by further processing of the measured ECG signal S2. For instance, the measured ECG signal S2 may be used for monitoring respiration of the subject. The further processing of the measured ECG signal S2 may be performed by an analysis module within the system 100. However, according to an alternative, the measured ECG signal S2 is output to an external unit for further processing.

The system 100 further comprises an electrical signal measurement module 20B. The electrical signal measurement module 20B may be configured to receive a set of voltage input signals representing voltages generated by the current signal S1 applied to the subject. The electrical signal measurement module 20B may be configured to extract a measured electrical signal S3 from the received set of voltage input signals.

The electrical signal measurement module 20B may comprise settings, which may be used for controlling the extraction of the electrical signal S3 from the received voltage input signals. For instance, a gain of the measured electrical signal S3 may be controlled by the settings.

The electrical signal measurement module 20B may be configured to process the received voltage input signals, e.g. by filtering the input signals, in order to extract relevant information. The filtering of the input signals may also be controlled by settings of the electrical signal measurement module 20B or may be performed according to a fixed set-up.

The electrical signal measurement module 20B may output the measured bioimpedance signal S3, which may be used for determining a condition of the subject by further processing of the measured electrical signal S3. For instance, the measured electrical signal S3 may be used for monitoring respiration of the subject. The further processing of the measured electrical signal S3 may be performed by an analysis module within the system 100. However, according to an alternative, the measured bioimpedance signal S3 is output to an external unit for further processing.

The system 100 further comprises a data quality detection module 30, which is configured to receive the measured ECG signal and the electrical signal S3. The data quality detection module 30 may be configured to detect an AC level and/or a DC level of the measured ECG signal and/or the electrical signal S3.

The data quality detection module 30 may further store an AC reference value range and/or a DC reference value range for the ECG signal S2 and/or the electrical signal S3. The AC reference value ranges and/or the DC reference value ranges may be set to define acceptable AC levels and DC levels, respectively, for high quality data acquisition. Alternatively, the AC reference value ranges and/or the DC reference value ranges may be set to define non-acceptable AC levels and DC levels, respectively, for high quality acquisition.

The data quality detection module 30 may be configured to detect whether the AC level and/or the DC level of the measured ECG signal S2 and the electrical signal S3 is within or outside the AC reference value ranges and the DC reference value ranges, respectively. For instance, the data quality detection module 30 may compare the detected AC level and/or the detected DC level to the AC reference value range and the DC reference value range, respectively.

In this way, the data quality detection module 30 may be configured to determine whether data quality is not within acceptable limits, based on the relation of the AC level and/or the DC level to the AC reference value range and the DC reference value range, respectively.

When the data quality detection module 30 detects that the measured ECG signal S2 or the electrical signal S3 is of a non-acceptable data quality, a control signal CS1 may be output by the data quality detection module 30.

The system 100 further comprises a signal adaptation module 40, which is configured for modifying at least one parameter of the current signal injection module 10 and/or the ECG signal measurement module 20A and/or the electrical signal measurement module 20B. The control signal CS1 from the data quality detection module 30 may be received by the signal adaption module 40. The signal adaptation module 40 may thus be configured to cause a change settings of the system 100 so as to adaptively change the system 100. The changing of the settings may ensure that a high quality ECG signal S2 and/or that a high quality electrical signal S3 is acquired even if conditions in which the ECG signal S2 and/or the electrical signal S3 is acquired have changed.

The signal adaptation module 40 may be configured for modifying at least one parameter of the current signal injection module 10 and/or the ECG signal measurement module 20A and/or the electrical signal measurement module 20B based on whether the AC level and/or the DC level of the measured ECG signal S2 and/or the measured electrical signal S3 is within or outside the AC reference value range and the DC reference value range, respectively. This implies that the AC level and/or the DC level of the measured ECG signal S2 and/or the electrical signal S3 may be used as quality measure(s) of the ECG signal acquisition and the electrical signal acquisition, and the signal adaptation module 40 may be configured to perform parameter modification based on the quality measure(s).

The signal adaptation module 40 may be configured to send parameter modification signals to the current signal injection module 10 and/or the ECG signal measurement module 20A and/or the electrical signal measurement module 20B. The parameter modification signal may comprise information that a parameter is to be modified and may comprise a new value of the parameter. Alternatively, the parameter modification signal may indicate whether a value of the parameter is to be increased or decreased.

The signal adaptation module 40 may be configured to modify at least one of an amplitude of the generated current signal S1, a frequency of the generated current signal S1, and a gain of the measured ECG signal S2 and/or the measured electrical signal S3.

The system 100 may further comprise electrodes 70, which may be integrated with the system 100 and may be connected to the current signal injection module 10, the ECG signal measurement module 20A and the electrical signal measurement module 20B. Alternatively, the electrodes 70 may be configured to be connected to the system 100.

The electrodes 70 may be configured to be attached to the subject for applying the current signal S1 to the subject and for detecting a voltage generated by the current S1 passing through tissue of the subject. Moreover, the same set, or a different set, of electrodes may be configured to be attached to the subject for detecting a voltage generated by the electrical activity of the subject's heart. Two or more electrodes 70 may be used and the electrodes 70 may be configured for injecting the current signal S1 and detecting a voltage by the same or by different electrodes 70. Having more than two electrodes 70 may also allow selectively choosing which electrodes 70 that should be part of the pair(s) used for injecting the current signal S1 and detecting the voltage generated by the current signal S1.

The signal adaptation module 40 may further be configured to select which electrodes 70 that are to be included in the electrode pair for measuring the ECG signal S2 and/or the electrical signal S3. The signal adaptation module 40 may in this regard send a parameter modification signal to the ECG signal measurement module 20A and/or the electrical signal measurement module 20B for controlling which input signals that are to be selected by ECG signal measurement module 20A and the electrical signal measurement module 20B, respectively.

During a process of parameter modification, the signal adaptation module 40 may send parameter modification signals to the current signal injection module 10 and/or the ECG signal measurement module 20A and/or the electrical signal measurement module 20B. Then, a quality of the measured ECG signal S2 and/or the electrical signal S3 based on changed parameters, may be detected in the data quality detection module 30. As long as the quality is not acceptable, at least one parameter may be continuously modified by further parameter modification signals from the signal adaptation module 40. When an acceptable data quality is detected by the data quality detection module 30, a new control signal CS1 may be sent to the signal adaptation module 40 terminating the process of parameter modification.

The AC reference value range and the DC reference value range may also be changed in association with parameter modification. For instance, if the parameter modification process results in that a best possible signal quality is not within desired ranges, the AC reference value range and the DC reference value range may be changed such that the data quality detection module will not constantly trigger a parameter modification. This may allow acquiring bioimpedance signal of a relatively high quality. When it is detected that a higher quality signal may again be acquired, the AC reference value range and the DC reference value range may again be changed for controlling the system to acquire signal quality within desired ranges.

The data quality detection module 30 may be configured to continuously detect quality of the measured ECG signal S2 and/or the electrical signal S3. Thus, as soon as signal quality deteriorates, this may be detected in the data quality detection module 30.

Alternatively, the data quality detection module 30 may be configured to detect quality at predetermined intervals. This may be regular intervals or intervals depending on input that may indicate a likelihood of data quality deteriorating. By the data quality detection module 30 detecting quality at intervals, data processing power may be saved, while allowing detection of unacceptable data quality fairly quickly. For instance, the data quality detection module 30 may detect quality every 10 seconds.

Adaptation of the system 100 for ECG signal acquisition and/or electrical signal acquisition may be needed when the subject changes posture. The posture change may for instance affect a relation between electrodes 70 and/or between electrodes 70 and the subject. Thus, a posture change may often be associated with a need of adapting the system 100.

The system 100 may further comprise a posture detection module 50. The posture detection module 50 may be configured to receive information relevant to a subject's posture from a sensor, such as an accelerometer mounted on the subject and/or a camera monitoring a scene in which the subject is located. The posture detection module 50 may be configured to process the information in order to determine a posture of the subject.

The posture detection module 50 need not necessarily determine an absolute posture of the subject. According to an alternative, the posture detection module 50 may be configured to determine that a posture change occurs.

When the posture detection module 50 determines a changed posture (or a change in posture), the posture detection module 50 may provide a signal to the signal adaptation module 40 in order to trigger parameter modification. Alternatively, or additionally, the posture detection module 50 may provide a signal to the data quality detection module 30 in order to trigger checking of quality of the measured ECG signal S2 and/or the electrical signal S3, which may in turn trigger parameter modification.

The system 100 may be calibrated to adapt the system 100 to a subject 200. Thus, the system 100 may be personalized and parameters for acquiring ECG signals and electrical signals of high quality for the subject may be determined. The parameters may differ substantially between different subjects, e.g. since bioimpedance may vary between different subjects. Also, the parameters may differ depending on placement of electrodes on the subject, so calibration may be needed before each session of bioimpedance signal acquisition, even for the same subject.

Results of the calibration may be stored in a memory within the system 100. Thus, parameters may be retrieved from the memory. The calibration may be performed based on different postures, such that when a change to a specific posture is detected by the posture detection module 50, parameters for the specific posture may be retrieved from the memory. Thus, the system 100 may immediately be set to use parameters, which should enable the system 100 to acquire the measured ECG signal S2 and/or the electrical signal S3 with a high quality for the changed posture. This may imply setting at least one of the amplitude of the current signal S1, the frequency of the signal S1, the gain of the measured ECG signal S2 and/or the measured electrical signal S3 and the electrodes to be included in the electrode pair for measuring the ECG signal S2 and/or the electrical signal S3. Also, setting the parameters may include setting the AC reference value range and the DC reference value range to be used by the data quality detection module 30.

The calibration need not beforehand determine settings for different postures. The settings may alternatively be determined when a posture is first detected and, then, the settings for the posture may be stored in order to enable re-use.

The data quality detection module 30 may be configured to detect whether the change to parameters does provide an output of a high quality measured bioimpedance signal S3. If not, further parameter modification may be triggered.

The system 100 may comprise a memory, which may store the calibration data. The memory may be accessible for each of the current signal injection module 10, the bioimpedance signal measurement module 20A, the data quality detection module 30 in order to retrieve settings for the modules. Alternatively, or additionally, the memory may be accessible by the signal adaptation module 40, which may then send information of the settings to the other modules. The system 100 may comprise a single memory which is accessible by the modules. Alternatively, each module may comprise an internal memory which stores calibration data relevant for that module.

The system 100 may comprise a pulse wave generating module 60. The pulse wave generating module 60 may be configured to receive the ECG signal S2 and the electrical signal S3 and determine a pulse wave signal PWS in accordance with the method of the first aspect of the invention, or any embodiments thereof. In particular, the pulse wave generating module 60 may be configured to determine a cleaned electrical signal S4 in accordance with the method M100, and determine the pulse wave signal PWS by subtracting the cleaned electrical signal S4 from the electrical signal S3, thereby providing a pulse wave signal PWS. The pulse wave generating module 60 may be configured to filter the pulse wave signal PWS and taking its absolute value. The pulse wave generating module 60 may be configured to receive a control signal CS2 for controlling how the pulse wave signal PWS is determined and obtained. Moreover, the pulse wave generating module 60 may be configured to receive a blood pressure measurement and calibrate the pulse wave signal in terms of blood pressure. The pulse wave generating module 60 may be configured to output a pulse wave signal PWS.

The system 100 may further comprise a cardiovascular parameter determination module 80. The cardiovascular parameter determination module 80 may be configured to determine one or more cardiovascular parameters, such as PAR values. The cardiovascular parameter determination module 80 may be configured to receive the pulse wave signal PWS from the pulse wave generating module 60 and determine the PAR value. The cardiovascular parameter determination module 80 may be configured to output the PAR value. Moreover, the cardiovascular parameter determination module may be controlled by a control signal CS3 from the data quality detection module 30.

Each of the modules 10, 20A, 20B 30, 40, 50, 60, 80 may be implemented in hardware, or as any combination of software and hardware. At least part of the modules 10, 20A, 20B, 30, 40, 50, 60, 80 may, for instance, be implemented as software being executed on a general-purpose computer. The system 100 may thus comprise one or more processing units, such as a central processing unit (CPU), which may execute the instructions of one or more computer programs in order to implement functionality of the modules. Thus, the system 100 may comprise a single processing unit, which may provide functionality of each of the modules 10, 20A, 20B, 30, 40, 50, 60, 80 e.g. as separate threads within the processing unit.

The modules 10, 20A, 20B, 30, 40, 50, 60 may alternatively be implemented as firmware arranged e.g. in an embedded system, or as a specifically designed processing unit, such as an Application-Specific Integrated Circuit (ASIC) or a Field-Programmable Gate Array (FPGA).

The current signal injection module 10 may comprise circuitry for converting control instructions, which may be implemented in software and/or hardware, to an actual current signal 51, which may be output to electrodes 70 for being applied to a subject.

The ECG signal measurement module 20A may comprise circuitry for converting control instructions, which may be implemented in software and/or hardware, to form a ECG signal S2 based on received input voltage signals.

The electrical signal measurement module 20B may comprise circuitry for converting control instructions, which may be implemented in software and/or hardware, to form an electrical signal S3 based on received input voltage signals.

The system 100 may comprise a housing, in which the modules 10, 20A, 20B, 30, 40, 50, 60, 80 may be arranged. The system 100 may thus be delivered in a single package and may comprise an interface for putting the system 100 into use.

The housing may for instance comprise ports, to which electrodes 70 may be connected for receiving the current signal S1 and providing voltage signals representing a bioimpedance. Alternatively, electrodes 70 may be pre-attached to the housing on delivery of the system 100. The electrodes 70 may be arranged to the housing.

The housing may further comprise an output port for connection to an external unit, which may receive the measured electrical signal S3 for further processing of the signal. Alternatively, or additionally, the housing may comprise a communication unit for wireless communication of the electrical signal S3 to the external unit.

The housing may further comprise additional ports for connecting further units to the system 100, such as one or more sensors for detecting posture of the subject. The housing may be configured to be worn by a subject 200, such that the system 100 allowing acquisition of the measured ECG signal S2 and/or the electrical signal S3 with high quality may be worn and used for long-term monitoring of the subject. The housing may comprise a strap for attaching the housing to or around a body part of the subject 200 or may have a shape so as to allow the housing to be worn by the subject 200. The housing may be adhesively attached to or around a body part of the subject 200. The housing may be a patch-like structure. The housing may be adapted to be conformable to a subject's body, and may be made in a flexible material. Alternatively, the housing may be configured for being implanted in a subject 200.

Moreover, the system 100 may be configured to communicate with other medical equipment, such as an intensive care unit or a pacemaker. The communication may be performed by wired means or wirelessly. The system 100 may be configured to generate a control signal based on a determined pulse wave signal PWS, a pulse amplitude ratio PAR, or other cardiovascular parameters, which is used to control the operative state of the intensive care unit or the pacemaker.

Hence, the breathing and heart rate may be controlled in accordance with the information acquired by the system 100.

FIG. 13a illustrates an ECG signal with points of interest that may be used in determining a pulse wave signal according to some embodiments of the invention. Although, at least one of the points of interests in the ECG-signal may correspond to the R-peak, other discernable feature in the ECG-signal may be used as well, either instead of or in combination with the R-peak. Such a discernible feature may be a peak in the ECG signal, for instance, the R-peak, the P-peak, or the T-peak, or a dip in the ECG signal, for instance the Q-dip or the S-dip. For instance, two or more of these discernable features for every heartbeat response indicated in the ECG-signal.

Moreover, the point or points of interest selected for every heartbeat response indicated in the ECG-signal may be selected based on predetermined priority of selection assigned to the discernable features in the ECG-signal. By this, it is meant that the method prioritizes one particular type of discernable feature and when that particular type of discernable feature is not detected for a heartbeat response in the ECG-signal, the method will look for another particular type of discernable feature of lesser priority in the ECG signal.

The priority of selection may be determined based on some predetermined rule, for instance, the priority of selection may be based on amplitude from a baseline of the ECG-signal. For instance, the R-peak may be assigned the highest priority of selection. The remaining discernable features may be assigned a lesser priority of selection, for instance in the following decreasing order: T-peak, S-dip, P-peak, Q-dip.

FIGS. 13b-13d illustrate a pulse wave signal indicating how the specific points in the electrical signal are selected according to some embodiments of the invention. The specific points in the electrical signal are selected to correspond to zero or near zero blood-flow in the pulse wave signal. FIG. 13b indicates in one embodiment when it this occurs, see region denoted PWS0. The start point PWS01 of this region PWS0 may correspond to a first selected specific point S3x1 in the electrical signal S3 and the end point PWS01 of this region PWS0 may correspond to a second selected specific point S3x2 in the electrical signal S3. The method may adjust the time offset of the specific points S3x1, S3x2 in the electrical signal relative points of interests S2x in the ECG-signal, so that the specific points S3x1, S3x2 are selected to meet the condition of zero or near zero blood flow in the pulse wave signal PWS. One option to find the region PWS0 in the pulse wave signal PWS is to look for a point PWS03 corresponding to the point characterized by the steepest slope of the pulse wave signal PWS, see FIG. 13d. In the drawings and specification, there have been disclosed preferred embodiments and examples of the invention and, although specific terms are employed, they are used in a generic and descriptive sense only and not for the purpose of limitation, the scope of the invention being set forth in the following claims.

The invention claimed is:

1. A method, comprising:

attaching a patch unit to a torso of a subject, the patch unit comprising one or more first sensors and one or more second sensors, wherein at least one of the one or more first or second sensors comprises an electrode;

measuring an electrocardiographic, ECG, signal of the subject using the one or more first sensors, wherein the ECG signal indicates two or more consecutive heartbeat response cycles;

measuring an electrical signal of the subject using the one or more second sensors;

determining a collection of points of interest in the ECG signal, wherein the points of interest comprise: peaks, dips, or where a slope of the ECG signal reaches a predetermined threshold;

determining a collection of specific points in the electrical signal based on the collection of points of interest in the ECG signal as a starting point, wherein the specific points in the electrical signal comprise: peaks, dips, local maxima, or local minima, and wherein the determined collection of specific points includes two or more specific points in the electrical signal for every heartbeat response cycle indicated in the ECG signal;

determining a cleaned electrical signal based on the collection of specific points in the electrical signal;

generating a pulse wave signal by subtracting the cleaned electrical signal from the electrical signal; and determining at least one cardiovascular parameter of the subject based on the generated pulse wave signal, wherein the at least one cardiovascular parameter comprises at least one of: pulse amplitude ratio, arterial blood pressure, pulse transit time, arterial stiffness, left ventricular end diastolic volume pressure, or pulmonary capillary wedge pressure, and wherein the collection of specific points in the electrical signal is determined based on timestamps of the collection of points of interest in the ECG signal, and wherein at least one of the two or more specific points in the electrical signal for every heartbeat response cycle indicated in the ECG signal is associated with a timestamp offset in time relative to the timestamp of a corresponding point of interest in the ECG signal, the timestamp offset being a time difference between the corresponding point of interest in the ECG signal and the at least one specific point in the electrical signal.

2. The method according to claim 1, wherein the two or more specific points in the electrical signal for every heartbeat response cycle indicated in the ECG signal are determined based on either one point of interest for every heartbeat response cycle indicated in the ECG signal, or a plurality of corresponding points of interest for every heartbeat response cycle indicated in the ECG signal.

3. The method according to claim 1, wherein the points of interest are determined within a predetermined time window in the ECG signal.

4. The method according to claim 1, wherein the cleaned electrical signal is determined using interpolation based on the collection of specific points.

5. The method according to claim 1, further comprising filtering the pulse wave signal and taking the absolute value of the filtered pulse wave signal.

6. The method according to claim 1, wherein the pulse wave signal is generated continuously while the ECG signal and the electrical signal are being measured.

7. The method according to claim 1, wherein a measurement device comprises the patch unit, and wherein the method further comprises positioning the measurement device fixedly to the torso of the subject to measure the ECG signal and the electrical signal using electrodes of the patch unit.

8. The method according to claim 7, wherein the measurement device is positioned so that the generated pulse wave signal is associated with a specific portion of a circulatory system of the subject.

9. The method according to claim 8, wherein the specific portion of the circulatory system of the subject is selected from the group consisting of the aorta, the pulmonary artery, and the abdominal artery.

10. The method according to claim 1, further comprising calibrating the generated pulse wave signal using a blood pressure measurement, and measuring the blood pressure of the subject.

11. The method according to claim 1, further comprising:

outputting the generated pulse wave signal, and monitoring a heart rate and/or cardiovascular parameters of the subject based on the output pulse wave signal.

12. The method according to claim 1, wherein the patch unit is adapted to be adhesively attached to the torso of the subject.

13. A system, comprising:

a measurement device comprising a patch unit configured to be attached to a torso of a subject, the patch unit comprising a first plurality of sensors and a second plurality of sensors, wherein the first plurality of sensors are adapted to measure an electrocardiographic, ECG, signal of the subject, and the second plurality of sensors are adapted to measure an electrical signal of the subject, wherein the ECG signal of the subject indicates two or more consecutive heartbeat response cycles, and wherein at least one of the first or second plurality of sensors comprises an electrode; and a processing unit configured to receive the ECG signal and the electrical signal, wherein the processing unit is further configured to:

determine a collection of points of interest in the ECG signal, wherein the points of interest comprise: peaks, dips, or where a slope of the ECG signal reaches a predetermined threshold, determine a collection of specific points in the electrical signal based on the collection of points of interest in the ECG signal as a starting point, wherein the specific points in the electrical signal comprise: peaks, dips, local maxima, or local minima, and wherein the determined collection of specific points includes two or more specific points in the electrical signal for the heartbeat response cycles indicated in the ECG signal, determine a cleaned electrical signal based on the collection of specific points in the electrical signal, generate a pulse wave signal by subtracting the cleaned electrical signal from the electrical signal, and determine at least one cardiovascular parameter of the subject based on the generated pulse wave signal, wherein the at least one cardiovascular parameter comprises at least one of: pulse amplitude ratio, arterial blood pressure, pulse transit time, arterial stiffness, left ventricular end diastolic volume pressure, or pulmonary capillary wedge pressure, wherein the collection of specific points in the electrical signal are determined based on timestamps of the collection of points of interest in the ECG signal, and wherein at least one of the two or more specific points in the electrical signal for every heartbeat response cycle indicated in the ECG signal is associated with a timestamp offset in time relative to the timestamp of the corresponding point of interest in the ECG signal, the timestamp offset being a time difference between the corresponding point of interest in the ECG signal and the at least one specific point in the electrical signal.

14. The system according to claim 13, wherein the first plurality of sensors and the second plurality of sensors of the measurement device both comprise electrodes.

15. The system according to claim 14, wherein the ECG signal and the electrical signal are measured using the same electrodes.

16. The system according to claim 13, wherein the patch unit is adapted to be adhesively attached to the torso of the subject.

17. The system according to claim 13, wherein the processing unit is further configured to determine the cleaned electrical signal using interpolation based on the collection of specific points.

18. The system according to claim 13, wherein the processing unit is further configured to generate the pulse wave signal while the ECG signal and the electrical signal are being measured.

19. The system according to claim 13, wherein the processing unit is further configured to calibrate the generated pulse wave signal using a blood pressure measurement, and to measure the blood pressure of the subject.

20. A system, comprising an implantable measurement device comprising a first plurality of sensors and a second plurality of sensors, wherein the first plurality of sensors are adapted to measure an electrocardiographic, ECG, signal of a subject, and the second plurality of sensors are adapted to measure an electrical signal of the subject, wherein the ECG signal of the subject indicates two or more consecutive heartbeat response cycles, and wherein at least one of the first or second plurality of sensors comprises an electrode; and a processing unit configured to receive the ECG signal and the electrical signal, wherein the processing unit is further configured to:

determine a collection of points of interest in the ECG signal, wherein the points of interest comprise: peaks, dips, or where a slope of the ECG signal reaches a predetermined threshold, determine a collection of specific points in the electrical signal based on the collection of points of interest in the ECG signal as a starting point, wherein the specific points in the electrical signal comprise: peaks, dips, local maxima, or local minima, and wherein the determined collection of specific points includes two or more specific points in the electrical signal for the heartbeat response cycles indicated in the ECG signal, determine a cleaned electrical signal based on the collection of specific points in the electrical signal, generate a pulse wave signal by subtracting the cleaned electrical signal from the electrical signal, and determine at least one cardiovascular parameter of the subject based on the generated pulse wave signal, wherein the at least one cardiovascular parameter comprises at least one of: pulse amplitude ratio, arterial blood pressure, pulse transit time, arterial stiffness, left ventricular end diastolic volume pressure, or pulmonary capillary wedge pressure, wherein the collection of specific points in the electrical signal are determined based on timestamps of the collection of points of interest in the ECG signal, and wherein at least one of the two or more specific points in the electrical signal for every heartbeat response cycle indicated in the ECG signal is associated with a timestamp offset in time relative to the timestamp of the corresponding point of interest in the ECG signal, the timestamp offset being a time difference between the corresponding point of interest in the ECG signal and the at least one specific point in the electrical signal.

* * * * *